United States Patent
Nakao et al.

(10) Patent No.: US 10,369,159 B2
(45) Date of Patent: Aug. 6, 2019

(54) ESTROGEN RECEPTOR β PARTIAL AGONIST HAVING ESTROGEN RECEPTOR α INHIBITORY EFFECT, AND GYNECOLOGICAL DISEASE THERAPEUTIC AGENT USING SAME

(71) Applicants: NOBELPHARMA CO., LTD., Tokyo (JP); NATIONAL UNIVERSITY CORPORATION TOTTORI UNIVERSITY, Tottori-shi, Tottori (JP)

(72) Inventors: Kenichiro Nakao, Tokyo (JP); Tasuku Harada, Tottori (JP); Fuminori Taniguchi, Tottori (JP)

(73) Assignees: Nobelpharma Co., Ltd., Tokyo (JP); National University Corporation Tottori University, Tottori (JP)

( * ) Notice: Subject to any disclaimer, the term of this patent is extended or adjusted under 35 U.S.C. 154(b) by 0 days.

(21) Appl. No.: 16/138,556

(22) Filed: Sep. 21, 2018

(65) Prior Publication Data
US 2019/0022111 A1 Jan. 24, 2019

Related U.S. Application Data

(63) Continuation of application No. 15/744,537, filed as application No. PCT/JP2016/070687 on Jul. 13, 2016.

(30) Foreign Application Priority Data

Jul. 14, 2015 (JP) .................................. 2015-140620

(51) Int. Cl.
*A61K 31/573* (2006.01)
*A61P 15/00* (2006.01)

(52) U.S. Cl.
CPC ............ *A61K 31/573* (2013.01); *A61P 15/00* (2018.01)

(58) Field of Classification Search
CPC ............................. A61K 31/573; A61P 15/00
USPC ......................................................... 514/182
See application file for complete search history.

(56) References Cited

U.S. PATENT DOCUMENTS

2013/0231292 A1 9/2013 Zhou et al.

FOREIGN PATENT DOCUMENTS

| WO | 99/33859 | 7/1999 |
|---|---|---|
| WO | 01/58919 | 8/2001 |
| WO | 2008/128791 | 10/2008 |
| WO | 2010/054758 | 5/2010 |

OTHER PUBLICATIONS

Minutolo, et al., "Estrogen Receptor B Ligands: Recent Advances and Biomedical Applications", Medicinal Research Reviews, vol. 31, No. 3, 2011, pp. 364-442.
Kulak Jr., et al., "Treatment with Bazedoxifene, a Selective Estrogen Receptor Modulator, Causes Regression of Endometriosis in a Mouse Model", Endocrinology, vol. 152, No. 8, 2011, pp. 3226-3232.
Chung, et al., The Effect of GnRH Agonist, SERM, Antiprogesterone in the Treatment of Uterine Myomas, Acta Obstetrica et Gynaecologia Japonica, vol. 65, No. 2, 2013, p. 994, ISP-5-5, cited in the English translation of the International Search Report.
Nozaki, "The effect of raloxifene on reproductive organs", Obstetrical and Gynecological Therapy, vol. 94, No. 5, 2007, pp. 967-972—English Abstract.
Taniguchi, et al., "SR-16234, a selective estrogen receptor modulator, represses development of endometriosis-like lesions in rat model", Acta Obstetrica et Gynaecologia Japonica, vol. 68, No. 2, Feb. 2016, p. 567 2016.
Yamamoto, et al., "TAS-108, a Novel Oral Steroidal Antiestrogenic Agent, Is a Pure Antagonist on Estrogen Receptor a and a Partial Agonist on Estrogen Receptor B with Low Uterotrophic Effect", Clinical Cancer Research, vol. 11, Jan. 2005, pp. 315-322.
Yamaya, et al., "Distribution of (7_)-21-[4-[(Diethylamino) Methyl]-2-Methoxyphenoxy]-7-Methyl-19-Norpregna-1,3,5 (10)-Trien-3-OL-20a-[14c]2-Hydroxy-1,2,3-Propanetricarboxylate ([14c]Tas-108) and Its Metabolites After Single Oral Administration to Rats Bearing 7,12-Dimethylbenz(a)Anthracene induced Mammary Tumor", Drug Metabolism and Disposition, vol. 34, No. 2, 2006, 331-338.
Yamamoto, et al., "Both N- and C-terminal transactivation functions of DNA-bound ERa are blocked by a novel synthetic estrogen ligand", Biochemical and Biophysical Research Communications, vol. 312, No. 3, 2003, pp. 656-662.
Blakely, et al., "A Phase I and Pharmacokinetic Study of TAS-108 in Postmenopausal Female Patients with Locally Advanced, Locally Recurrent Inoperable, or Progressive Metastatic Breast Cancer", Clinical Cancer Research, vol. 10, 2004, pp. 5425-5431.
Kumagai, et al., "Safety, Tolerability and Pharmacokinetics of TAS-108, a Novel Anti-Oestrogen, in Healthy Post-Menopausal Japanese Women: A Phase I Single Oral Dose Study", Basic & Clinical Pharmacology & Toxicology, vol. 104, 2009, pp. 352-359.
International Search Report issued in International Application No. PCT/JP2016/070687, dated Nov. 22, 2016, 4 pages.
Rose et al., Exacerbation of endometriosis as a result of premenopausal tamoxifen exposure, Am. J. Obstet. Gynecol. 2000; 183:507-8.
Ismail et al., Tamoxifen-associated post-menopausal endometriosis, Histopathology, 1997, 30, 187-191.
Stratton et al, Return of chronic pelvic pain from endometriosis after raloxifene treatment: A randomized controlled trial, Obstet Gynecol., 2008; 111:88-96.

(Continued)

*Primary Examiner* — Yevgeny Valenrod
(74) *Attorney, Agent, or Firm* — Hamre, Schumann, Mueller & Larson, P.C.

(57) ABSTRACT

[Problem] To provide a therapeutic agent for estrogen-dependent gynecological diseases such as endometriosis, uterine fibroids, and uterus adenomyosis. [Solution] To use an estrogen receptor α-inhibiting β partial agonist represented by the formula (a), a pharmaceutically-acceptable salt thereof, or a hydrate of either of the afore-mentioned, as an active ingredient.

4 Claims, 2 Drawing Sheets

(56) References Cited

OTHER PUBLICATIONS

Center for drug evaluation and research, application No. 020815, Pharmacological/Toxicological Review of NDA Submission, Raloxifene hydrochloride (Evista TM), Eli Lilly and Company, Nov. 21, 1997.
Premkumar et al., Gynecologic and hormonal effects of Raloxifene in premenopausal women, Fertility and Sterility 88: 1637-44, Dec. 2007.
Harada, et al., SR-16234, a Novel Selective Estrogen Receptor Modulator for Pain Symptoms with Endometriosis: An Open-label Clinical Trial, Yonago Acta Medica 2017; 60:227-233.
Koehler, et al., "Reflections on the Discovery and Significance of Estrogen Receptor [beta]", Endocrine Reviews, vol. 26, No. 3, May 1, 2005, pp. 465-478.
Supplementary European Search Report issued in corresponding European Application Serial No. 16824495.2, dated May 6, 2019, 7 pages.

ESTROGEN RECEPTOR β PARTIAL AGONIST HAVING ESTROGEN RECEPTOR α INHIBITORY EFFECT, AND GYNECOLOGICAL DISEASE THERAPEUTIC AGENT USING SAME

FIELD OF THE INVENTION

The present invention relates to an estrogen receptor β partial agonist having estrogen receptor α inhibitory effect, and a gynecological disease therapeutic agent using the same.

BACKGROUND OF THE INVENTION

There are diseases caused by abnormality of estrogen or progesterone as organic gynecological diseases. Examples of the diseases include endometriosis, uterine fibroids, and uterus adenomyosis.

As treatment of such diseases, administration of gonadotropin agonist (GnRH agonist), as a drug therapy, is known, however, a period for drug administration is restricted because of the side effects such as bone mineral loss and ovarian dysfunction symptoms, thus no gynecological disease therapeutic agents for long-term use have existed yet, and so surgical therapy such as surgical resection is still a first choice.

Therefore, for the treatment of gynecological disease, a drug effective for long-term administration to inhibit the growth of ectopic endometrial tissue and suppress or improve the intra-uterine fibroids and uterus adenomyosis has been desired. It has also been desired to relief pains such as lower abdominal pain and low back pain caused by these gynecological diseases.

Conventionally, as a drug to inhibit binding of estrogen to the receptor antagonist, tamoxifen (Registered Trademark: Nolvadex) with an indication of breast cancer has been used since the 1980s in Japan. However, it is reported that this drug causes uterine body cancer, uterine sarcoma or endometriosis, thus it may not be used to treat estrogen-dependent diseases including endometriosis. The mechanism of proliferative effects of the drug against the endometrium is caused by its endogenous partial agonistic action to the estrogen receptor.

Then, fulvestrant (Registered Trademark: Faslodex) was approved as a therapeutic agent for postmenopausal breast cancer. This drug, unlike tamoxifen, does not provide endogenous partial agonist action to the estrogen receptor. However, this drug has low gastrointestinal absorption rate as well as short half-life even when intravenously administrating, thus a high capacity intramuscularly administration is necessary, and thus the dosage form is intramuscular injection. Therefore, it will never be used orally for treating estrogen-dependent diseases.

Further, as a selective estrogen receptor modulator (hereinafter, sometimes abbreviated as "SERM"), raloxifene (Registered Trademark: Evista) has been approved with an indication for osteoporosis treatment. However, this drug is an osteoporosis therapeutic agent having a bone mass-increasing by estrogen receptor partial agonist activity, thus it will never be used for treating estrogen-dependent diseases, that is gynecological diseases caused by ectopic endometrial tissue growth such as endometriosis, uterine fibroids, and uterus adenomyosis.

Other selective estrogen receptor modulators, (7α)-21-[4-[(diethylamino) methyl]-2-methoxyphenoxy]-7-methyl-19-norpregna-1,3,5(10)-triene-3-ol or a pharmaceutically acceptable salt thereof, which have been developed as a breast cancer therapeutic agent, are known (see Patent documents 1 and 2).

PRIOR ART DOCUMENTS

Patent Documents

Patent document 1: WO 2001/058919
Patent document 2: WO 1999/033859

Non-Patent Documents

Non-patent document 1: Clinical Cancer Research, vol. 11, 315-322, 2005
Non-patent document 2: Metabolism and Disposition, vol. 34 (2), 331-338, 2006
Non-patent document 3: BBRC, vol. 312, 656-662, 2003
Non-patent document 4: Journal of Clinical Pharmacology and Therapeutics, vol. 30, 456-470, 2005
Non-patent document 5: Clinical Cancer Research, vol. 10, 5425-5431, 2004
Non-patent document 6: Basic & Clinical Pharmacology & Toxicology, vol. 104, 352-359, 2009
Non-patent document 7: Annals of Oncology, vol. 714, 1-6, 2009

SUMMARY OF THE INVENTION

Problem to be Solved by Invention

The objective of the present invention is to provide a therapeutic agent of estrogen-dependent gynecological diseases such as endometriosis, uterine fibroids, and uterus adenomyosis.

Means for Solving the Problem

As a result of intensive studies on the above problems, quite unexpectedly, the present inventors have found that the compound represented by the following formula (a) synthesized and clinically studied to treat breast cancers worked as an estrogen receptor α-inhibiting β partial agonist and showed an excellent therapeutic effect on estrogen-dependent gynecological diseases, and accomplished the present invention.

The present invention provides a specific embodiment described in the following (1) to (3).
(1) An estrogen receptor α-inhibiting β partial agonist represented by the following formula (a) represented by the following structural formula (a).

[Compound 1]

(2) A gynecological disease therapeutic agent comprising the estrogen receptor α inhibiting β partial agonist of the (1)

above, a pharmaceutically acceptable salt thereof, or a hydrate of either of the afore-mentioned as an active ingredient. (3) The gynecological disease therapeutic agent of the (2) above, wherein the gynecological disease comprises endometriosis, uterine fibroids, and/or uterus adenomyosis.

Further, the present invention provides a specific embodiment described in the following (4) to (8).
(4) A method for treating gynecological diseases; a method for treating endometriosis, uterine fibroids, and/or uterus adenomyosis; and a method for treating endometriosis, uterine fibroids, and/or uterus adenomyosis in premenopausal patients; comprising a step of administering the estrogen receptor α-inhibiting β partial agonist of the (1) above, a pharmaceutically acceptable salt thereof, or a hydrate of either of the afore-mentioned, as an active ingredient.
(5) A method for alleviating gynecological diseases; a method for alleviating endometriosis, uterine fibroids, and/or uterus adenomyosis; and a method for alleviating endometriosis, uterine fibroids, and/or uterus adenomyosis in premenopausal patients; comprising a step of administering the estrogen receptor α-inhibiting β partial agonist of the (1) above, a pharmaceutically acceptable salt thereof, or a hydrate of either of the afore-mentioned, as an active ingredient.
(6) A use of the estrogen receptor α-inhibiting β partial agonist of the (1) above, a pharmaceutically acceptable salt thereof, or a hydrate of either of the afore-mentioned for treating gynecological diseases; for treating endometriosis, uterine fibroids, and/or uterus adenomyosis; and for treating endometriosis, uterine fibroids, and/or uterus adenomyosis in premenopausal patients.
(7) A use of the estrogen receptor α-inhibiting β partial agonist of the (1) above, a pharmaceutically acceptable salt thereof, or a hydrate of either of the afore-mentioned for manufacturing therapeutic agents for treating gynecological diseases; for manufacturing therapeutic agents for treating endometriosis, uterine fibroids, and/or uterus adenomyosis; and for manufacturing therapeutic agents for treating endometriosis, uterine fibroids, and/or uterus adenomyosis in premenopausal patients.
(8) Oral formulations comprising the estrogen receptor α-inhibiting β partial agonist of the (1) or (2) above as an active ingredient.

Effect of the Invention

According to the present invention, a drug for treating estrogen-dependent gynecological diseases such as endometriosis, uterine fibroids, and uterus adenomyosis may be provided.

DESCRIPTION OF THE EMBODIMENTS

Hereinafter will be described in detail embodiments of the present invention, the following embodiments are examples for explaining the present invention, the present invention is not limited thereto, it can be practiced with various modifications without departing from the scope of the subject matter. In the present description, for example, reference numerical range of "1 to 100" is intended to include both of the upper limit value "100" and the lower limit value "1". In addition, the other numerical ranges are referred in the same manner.

(Estrogen Receptor α Inhibitors, Estrogen Receptor β Partial Agonists)

A compound represented by the following formula (a) used in the present invention is orally active, and has an estrogen receptor α inhibitory effect and an estrogen receptor β partial agonist action.

[Compound 2]

A compound represented by the above formula (a) used in the present invention may be used in free form, in pharmaceutically acceptable salt form, or in hydrate form. The pharmaceutically acceptable salts include, but are not limited to, inorganic salts such as hydrochloride, sulfate, nitrate, hydrobromide and phosphate; and organic salts such as acetate, trifluoroacetate, lactate, propionate, tartrate, glycolate, pyruvate, oxalate, malate, malonate, succinate, maleate, fumarate, tartrate, citrate, benzoate, cinnamate, mandelate, methanesulfonate, ethanesulfonate, p-toluenesulfonate and salicylic acid; among these salts, the organic salts are preferred, and citrate, fumarate, succinate, benzoate and malonic acid are more preferred, and citrate is yet more preferred (hereinafter, citrate of the compound of the present invention may be abbreviated to "SR16234").

The compound represented by the above formula (a) used in the present invention, a pharmaceutically acceptable salt thereof, and a hydrate thereof may be prepared, for example, according to the methods described in the Patent Documents 1 and 2.

The compound represented by the above formula (a), a pharmaceutically acceptable salt thereof, and a hydrate thereof, as shown in the examples below, has an anti-proliferative activity in ectopic endometrial tissue, which is stable for a long period of time. Further, those compounds can be administered orally with a low toxicity, and may be safely used even by premenopausal patients. Thus, the drugs of the present invention are especially useful as therapeutic agents for estrogen-dependent gynecological diseases such as endometriosis, uterine fibroids, and uterus adenomyosis.

(Gynecological Disease Therapeutic Agents)

The gynecological disease therapeutic agent of the present invention includes at least the compound represented by the formula (a), a pharmaceutically acceptable salt thereof, or a hydrate of either of the afore-mentioned, as an active ingredient. The gynecological therapeutic drug of the present invention may include other components as needed. Examples of the other components include, but are not limited to, pharmaceutical additives such as stabilizers, surfactants, plasticizers, lubricants, solubilizers, buffering agents, sweetening agents, substrates, adsorbents, taste masking agents, binders, suspending agents, antioxidants, brightening agents, coating agents, flavoring agents, fragrances, humectants, wetting modifiers, defoamers, chews, fresheners, coloring agents, sugar coating agents, isotonic agents, pH adjusting agents, softeners, emulsifiers, adhesives, adhesion enhancers, thickeners, thickening agents, foaming agents, excipients, dispersing agents, propellants, disintegrating agents, disintegrating aids, aromatics, desiccants, antiseptic agents, preservatives, soothing agents, solvents, dissolving agents, solubilizing agents and fluidizing agents.

A dosage form of the gynecological disease therapeutic agents of the present invention may be selected, but is not limited to, depending on the patients age, weight, diseases, symptoms or the degree of the diseases or symptoms. Examples of the dosage form include oral administration in tablets (including sublingual tablets and orally disintegrating tablets), granules, powders, solutions, syrups (including dry syrups), jelly and capsules (including soft capsules and microcapsules); and parental administration in injections (such as subcutaneous injections, intravenous injections, intramuscular injections and intraperitoneal injections), suppositories (including rectal suppositories and vaginal suppositories), inhalations, percutaneous formulations, eye drops and nasal drops. These may be controlled release formulation such as rapid-release formulation or sustained-release formulation. Among these formulations, oral administration in oral formulations is preferable from the view of easy to apply and medication compliance, and easy to reduce cost. As oral formulations, tablets, solutions and syrups are preferred, and tablets are more preferred.

A dosage amount of gynecological disease therapeutic agents of the present invention may be decided depending on the patients age, weight, diseases, symptoms or the degree of the diseases or symptoms. It is not particularly limited as long as pharmaceutically effective amount, but it may be, for oral formulation, in the range of 0.05 to 20 mg/kg body weight in free form in terms of the compound represented by the above formula (a), more preferably in the range of 0.06 to 18 mg/kg body weight, yet more preferably in the range of 0.07 to 17 mg/kg body weight, it may be preferable, for parental formulation, in the range of 0.001 to 10 mg/kg body weight, more preferably in the range of 0.002 to 9 mg/kg body weight, yet more preferably in the range of 0.003 to 8 mg/kg body weight.

The gynecological disease therapeutic agent of the present invention may be administered once or divided into several times. On administration, the dosage amount per day may be usually 0.1 to 5000 mg/kg, and a single dose or divided doses is desirable.

In a formulation of the gynecological disease therapeutic agent of the present invention, additives known in the art may be used, and methods known in the art, for example, methods described in the sixteenth Japanese Pharmacopoeia may be applied. For example, when preparing an oral solid formulation, to the active ingredient, excipients, binders, disintegrators, lubricants, coloring agents, taste masking agents or flavoring agents were added, followed by molded, granulated and encapsulated according to a conventional method to produce coated tablets, granules, powders, capsules, and the like. When preparing an oral liquid preparation, to the active ingredient, solvents such as purified water or ethanol, solubilizing agents, suspending agents, isotonic agents, taste masking agents, buffering agents, stabilizing agents or flavoring agents were added, followed by prepared and packed according to a conventional method to produce oral solutions, syrups, and the like. When preparing injections, to the active ingredient, pH adjusting agents, buffering agents, stabilizers, tonicity agents, or local anesthetics were added, followed by aseptically encapsulated into a container according to a conventional method to prepare subcutaneous, intramuscular, intravenous injections, and the like. When preparing rectal suppositories, to the active ingredient, excipients or surfactants were added, followed by mixed and molded according to a conventional method. When preparing formulations such as ointments, pastes, creams and gels, to the active ingredient, base materials such as white petrolatum and paraffin, stabilizers, wetting agents, or preservatives such as methyl parahydroxybenzoate were added, followed by mixed according to a conventional method. When preparing adhesive patches, to the support substrates such as woven fabrics, nonwoven fabrics, or plastic films, the ointments, creams, gels, pastes or the like may be applied by a conventional method.

The gynecological disease therapeutic agent of the present invention is targeted to estrogen-dependent gynecological diseases. As described above, since having anti-proliferative activity in ectopic endometrial tissues, targeting to endometriosis, uterine fibroids and uterus adenomyosis is preferred, and the agent may be safely used by premenopausal patients due to low toxicity. The agent may also alleviate or treat menorrhagia, irregular vaginal bleeding, dysmenorrhea, and pressure symptoms caused by these diseases.

EXAMPLES

Hereinafter, the present invention will be described in more detail by reference to the following various test results, but the invention should not be construed as being limited thereto.

Test Example 1: Confirmation of Endometriosis Inhibiting Activity

<Preparation of Endometriosis Model>
[1] Ovariectomy
1. Analgesic Treatment

Buprenorphine hydrochloride (Lepetan injection 0.3 mg, Otsuka Pharmaceutical Co., Ltd., 0.2 mg/mL of which was diluted to 6.7 times with a physiological saline solution to provide 0.03 mg/mL solution when using) was administered subcutaneously into the back of the rats at a dose of 0.0024 mg/body (0.08 mL/body). The administration period was two days, which includes twice before and after the model preparation on the day when the model was prepared, and twice per day on the next day. It should be noted that the dosage amount of 0.0024 mg/body was the one that satisfied a recommended dose of 0.01 mg/kg in 250 g-weight rat (0.0096 mg/kg) (estimated weight upon model preparation: 180 to 240 g).

2. Ovariectomy Method

Under 2% inhalation anesthesia, left and right flanks of the rats (operation site) were shaved, and the skin of one of the flasks was dissected. After peeling off the skin, the muscle layer was cut to open using a retractor so as to protrude it to the outside of the body with fat tissue around the ovary, then the fallopian tubes were ligated with a silk thread (sterile suture) followed by removing the ovary including the fat tissue. The peeled muscle layer and one part of the peritoneum were sutured with silk thread (sterile suture), then kanamycin solution, antibiotics, (manufactured by Meiji Seika Pharma Co., Ltd., "Meiji," kanamycin sulfate injection of 1000 mg was diluted to 5 mg/mL with injection solvent) was applied to the operation site. The dissected skin was sutured with silk thread (sterile suture). Another ovary in the opposite side was removed in the same manner. At the time of the operation, sterile gloves were used, and surgical instruments used were sterilized by an autoclave and beads sterilizer. The surgical area was shaved with an electric clipper followed by disinfected with isodine alcohol and covered with a sterile bedsheet and a covering cloth.

3. E2 Treatment

Since the day of ovariectomy, after it was performed, E2 (β-Estradiol, 3 μg/mL animal) was subcutaneously administered to the back of the rats every day for 2 weeks. E2 (3 μg/mL animal) was administered in the same manner during 4 weeks after model preparation on the date that the model was prepared.

[2] Grouping and Model Preparation

1. Grouping

Thirteen days after ovariectomy (day 0 counting), the rats were divided into four groups (N=8) as the total weight on the grouping day was uniform in each group. Animals excluded from the groups were distributed to the Sham group.

2. Method of Model Preparation

On the next day of the grouping, models were prepared in accordance with Uchiide et al method, which was partially modified Vernon et al method. Rats were placed under inhalation anesthesia of 2% isoflurane, and made an incision in the abdomen along the midline, then the right uterine horn was excised and cut in half along the vertical line after removing the fat cells around the excised uterine horn. The uterine horn was made an incision along the horizontal axis to cut out two strips of approximately 5 mm×5 mm. The serosal surface of the abdominal cavity and the endometrial surface of the uterus strips were faced and sawed up the four corners thereof with a bioabsorbable suture (6-0, PDS-II, manufactured by Ethicon) to graft the uterine horns into the right and left abdominal walls one by one. In order to avoid adhesion, the abdominal cavity was washed with saline (manufactured by Otsuka Pharmaceutical Factory). Then, the abdominal wall fascia was sawed up with a bioabsorbable suture (4-0, monocryl, manufactured by Ethicon) and the skin was sawed up with a silk suture (4-0, blade silk, manufactured by Ethicon).

[3] Sham Tissue Collection and Wet Weight Measurement

1. Dissection

On the previous day of the model preparation (the grouping date), under inhalation anesthesia of 2% isoflurane, an incision was made in the abdomen of the rats. Subsequently, about 5 mL of blood was collected with a syringe from the abdominal vena cava and collected in a Venoject II vacuum blood collection tube (EDTA-2K), then cut the abdominal vena cava and abdominal aorta to euthanize by exsanguination. The right uterine horn was excised and cut out two strips (approximately 5 mm×5 mm), then cut out strips (approximately 5 mm×5 mm) from the graft sites, the right and left abdominal walls (muscle layer and peritoneum). After that, wet weight of each strip and abdominal wall was measured. Then pituitary, adrenal glands (both sides), left uterine horn, mammary gland (excised with the nipples, three on the lower abdomen, a sample for RNA measurement was approximately 3 mm in diameter) and femur (left side) were excised.

2. EDTA Added Blood Treatment

The collected EDTA-added blood was centrifuged for 10 minutes at 4° C. at 1800×g to give plasma (2 mL or more). The obtained plasma was frozen and stored in an ultra-low temperature freezer.

3. Weight of Excised Organs

As for the pituitary, adrenal glands (both sides), left uterine horn and femur, wet weight was measured. The femur bone after wet weight measurement was discarded.

4. Treatment of Excised Organs

The pituitary, adrenal gland (right), uterine horn strip (approximately 5 mm mm), graft site abdominal walls (muscle layer and peritoneum, approximately 5 mm×5 mm) (one each), left uterine horn (portion collected from the above organs), and mammary glands (approximately 3 mm in diameter) were immersed in the RNA later solution and stored in a refrigerator for 1 day, then the RNA later solution was removed and stored in a very low temperature freezer (sample for RNA measurement). The remainder of the adrenal gland (right) was discarded, the remainder of the adrenal gland (left), mammary gland (one) and the remainder of each organ was frozen in liquid nitrogen.

5. Pathological Specimen

The mammary gland, the remaining uterine horn strip (approximately 5 mm×5 mm) and the graft site abdominal walls (muscle layer and peritoneum, approximately 5 mm×5 mm) (one each) were immersed in 10% neutral buffered formalin solution and fixed, respectively, then paraffin block-embedded specimens were prepared.

<Preparation and Administration of the Drug>

[1] Preparation Method (Undiluted Solution)

A required amount of SR16234 was weighed, pulverized with an agate mortar and pestle, and suspended in 0.5% carboxymethylcellulose sodium (CMC-Na) solution to prepare a 2 mg/mL solution, then used as undiluted solution. Preparation was performed using a volumetric flask. The obtained undiluted solution was stored in a cold place, in a refrigerator at the test substance storage room J009 (acceptable temperature range: 1 to 15° C.) after the preparation, then used within 7 days after the date of preparation. The remaining undiluted solution was discarded.

[2] Preparation Method (Solution for Administration)

The undiluted solution (2 mg/mL solution) was serially diluted with 0.5% CMC-Na aqueous solution to prepare 0.2, 0.06 and 0.02 mg/mL solution was respectively prepared. As a solution for administration for the vehicle control group, 0.5% CMC-Na aqueous solution was used. Preparation was carried out using a graduated cylinder or volumetric flask. The remaining undiluted solution was discarded.

[3] Drug Administration

The administration was made orally, and the drug was forcibly administered into a stomach once a day using a flexible oral sonde and syringe for 28 consecutive days.

<Evaluation of Endometriosis Inhibiting Activity>

[1] Dissection

On the next day of the final administration, the abdominal dissection was made under inhalation anesthesia of 2% isoflurane, and the grafted uterine strips (two pieces) were excised, and photographed with a digital camera. Subsequently, about 5 mL of blood was collected with a syringe from the abdominal vena cava and collected in a Venoject II vacuum blood collection tube (EDTA-2K), then cut the abdominal vena cava and abdominal aorta to euthanize by exsanguination. Then pituitary, adrenal glands (both sides), graft uterine strips (two pieces), left uterine horn, mammary gland (excised with the nipples, three on the lower abdomen, a sample for RNA measurement was approximately 3 mm in diameter) and femur (left side) were excised.

[2] Photography

The grafted uterine strips were photographed with a digital camera one by one along with a ruler.

[3] EDTA Added Blood Treatment

The collected EDTA-added blood was centrifuged for 10 minutes at 4° C. at 1800×g to give plasma (2 mL or more). The obtained plasma was frozen and stored in an ultra-low temperature freezer.

[4] Weight of the Excised Organs

As for the pituitary, adrenal glands (both sides), grafted uterine strip (one piece), left uterine horn and femur, wet weight was measured. The femur bone after wet weight measurement was discarded.

[5] Treatment of the Excised Organs

The pituitary, adrenal glands (right), graft uterine horn (one piece), left uterine horn (portion collected from the above organs), and mammary gland (approximately 3 mm in diameter) were immersed in the RNA later solution and stored in a refrigerator for 1 day, then the RNA later solution was removed and stored in a very low temperature freezer (sample for RNA measurement). The remainder of the adrenal gland (right) was discarded, the adrenal gland (left), mammary gland (one) and the remainder of each organ were frozen in liquid nitrogen.

[6] Pathological Specimen

The mammary gland and the rest of the grafted uterine strip (one piece) were immersion-fixed in 10% neutral buffered formalin solution to prepare a paraffin block-embedded specimen.

[7] Data Analysis

1. Calculation of Wet Weight of the Grafted Uterine Strips

The wet weight of each grafted uterine strip (left and right) was calculated by subtracting the average value of the wet weight of the left and right abdominal walls in the Sham group.

2. Calculation of Suppression Rate (%) of the Grafted Uterine Strip Weight

The suppression rate of the grafted uterine strip weight was calculated on the basis of the total average wet weight of the left and grafted uterine strips. Here, using the average wet weight of the grafted uterine strip in the vehicle control group as a basis, the suppression rate (%) of the grafted uterine strip weight in the vehicle control group and test sample group was calculated based on the following equation. The calculation results are shown in Table 1. Suppression rate of grafted uterine strip weight (%)=(average wet weight of the grafted uterine strip in the vehicle control group−wet weight of the grafted uterine strip of each individual)×100/(average wet weight of the grafted uterine strip in the vehicle control group)

TABLE 1

| Group | Suppression rate (% ± SE) |
| --- | --- |
| Vehicle control group | 0.0 ± 19.0 |
| SR16234 0.1 mg/kg p.o. | 36.4 ± 25.2 |
| SR16234 0.3 mg/kg p.o. | 63.2 ± 17.7 |
| SR16234 1.0 mg/kg p.o. | 97.7 ± 21.2 |

3. Suppression Rate of the Grafted Uterine Strip Weight

The suppression rate of the grafted uterine strip in the vehicle control group after administering 0.5 w/v % of sodium carboxymethyl cellulose aqueous solution (0.5% CMC—Na aqueous solution) was set as 0% to calculate the suppression rate of the grafted uterine strip (average value) in the 0.1, 0.3 and 1.0 mg/kg SR16234 administered groups, so that it was 26%, 45%, and 68%, respectively.

TABLE 2

| Group | Suppression rate (%) |
| --- | --- |
| Vehicle control group | 0.0 |
| SR16234 0.1 mg/kg p.o. | 26.0 |
| SR16234 0.3 mg/kg p.o. | 45.0 |
| SR16234 1.0 mg/kg p.o. | 69.0 |

As shown in Table 2, the increase suppression rate of the grafted uterine strip weight of SR16234 administered group was increased with increasing dose. Especially, the 1.0 mg/kg administered group showed a particularly significant suppression rate of the grafted uterine strip weight compared to the vehicle control group. From the observation above, it was confirmed an improving effect on endometriosis by the gynecological diseases therapeutic agent of the present invention.

Test Example 2: Confirmation of Endometriosis Inhibiting Activity in the Endometriosis Model <Total Wet Weight of the Grafted Uterine Strip and the Abdominal Wall>

A total wet weight of the left and right uterine strips and abdominal wall in the Sham group was 0.2596 g. In addition, a total wet weight of the left and right grafted uterine strips (including the abdominal wall) in the vehicle control group and 0.1, 0.3 and 1.0 mg/kg SR16234 administered groups was respectively 0.4785 g, 0.3988 g, 0.3401 g and 0.2647 g.

After the ovariectomy, 3 μg/mL/animal of E2 (β-Estradiol) was subcutaneously administered to the rats every day to maintain hormone balance, then using the rats, it was examined the improving effect by administration of SR16234 to "the endometriosis model" with transplanted the right uterine horn to the left and right abdominal walls. Administration of SR16234 was made orally once per day with three doses of 0.1, 0.3 and 1.0 mg/kg for consecutive 28 days from the day when the endometriosis model was prepared.

TABLE 3

| Group | Total wet weight of the grafted uterine strips (g) |
| --- | --- |
| Vehicle control group | 0.4785 |
| SR16234 0.1 mg/kg p.o. | 0.3988 |
| SR16234 0.3 mg/kg p.o. | 0.3401 |
| SR16234 1.0 mg/kg p.o. | 0.2647 |

As shown in Table 3, the total wet weight of the grafted uterine strips (including abdominal wall) in the SR16234 administered group is decreased with increasing dose. Especially, 1.0 mg/kg SR16234 administered group shows a particularly significant suppression ratio as compared to the vehicle control group. From the above, it was confirmed the improving effect by administration of the gynecological disease therapeutic agents of the present invention on the ovariectomized rat endometriosis model.

Test Example 3: Confirmation of Activities to the Bone Weight, Uterine Weight, and Pituitary Weight <Wet Weight of each Organ>
[1] Sham Group
The wet weight of pituitary, adrenal gland (left), adrenal gland (right), adrenal glands (the sum of the left and right), left uterine horn and femur (left) in the Sham group was 0.0186 g, 0.0353 g, 0.0296 g, 0.0649 g, 0.1751 g and 0.7083 g, respectively.
[2] Vehicle Control Group
The wet weight of pituitary, adrenal gland (left), adrenal gland (right), adrenal glands (the sum of the left and right), left uterine horn and femur (left) in the vehicle control group was 0.0271 g, 0.0468 g, 0.0425 g, 0.0893 g, 0.1428 g and 0.7589 g, respectively.
[3] 0.1 mg/kg SR16234 Administered Group
The wet weight of pituitary, adrenal gland (left), adrenal gland (right), adrenal glands (the sum of the left and right), left uterine horn and femur (left) in the 0.1 mg/kg SR16234 administered group was 0.0226 g, 0.0438 g, 0.0400 g, 0.0838 g, 0.1261 g and 0.7597 g, respectively.
[4] 0.3 mg/kg SR16234 Administered Group
The wet weight of pituitary, adrenal gland (left), adrenal gland (right), adrenal glands (the sum of the left and right), left uterine horn and femur (left) in the 0.3 mg/kg SR16234 administered group was 0.0187 g, 0.0398 g, 0.0381 g, 0.0779 g, 0.1119 g and 0.7598 g, respectively.
[5] 1.0 mg/kg SR16234 Administered Group
The wet weight of pituitary, adrenal gland (left), adrenal gland (right), adrenal glands (the sum of the left and right), left uterine horn and femur (left) in the 1.0 mg/kg SR16234 administered group was 0.0174 g, 0.0375 g, 0.0357 g, 0.0732 g, 0.1016 g and 0.7301 g, respectively.
[6] Results
It was confirmed that the SR16234 administered groups exhibited a decreasing trend associated with the dose increase in comparison with the vehicle control group. It was also confirmed that 0.3 mg/kg and 0.1 mg/kg SR16234 administered group exhibited a very mild weight suppression trend in comparison with the vehicle control group after the Day 14.

Test Example 4: Effects on Gene Expression of the Endometriosis Model

<Gene Expression Analysis of Endometrial Implants>
[1] Summary
Total RNA was extracted from 8 target genes of the rat-derived endometrial graft (27 specimens), then quality of the RNA was inspected with a spectrophotometer and bioanalyzer, and then reverse transcription reaction of the RNA was performed, followed by gene expression analysis was performed according to TaqMan method.
1. Main Instruments used in the Test
   NanoDrop 1000 (manufactured by Thermo Fisher Scientific)
   Agilent 2100 Bioanalyzer (manufactured by Agilent)
   Step One Plus Real-Time PCR System (manufactured by Life Technologies)
2. Main Reagents and Apparatus used in the Test
<RNA Extraction Reagent>
   RNeasy Fibrous Tissue Mini Kit (Manufactured by QIAGEN)
<Reverse Transcriptase>
   SuperScript VILO Master Mix (manufactured by Life Technologies)

<TaqMan Reagent>
   TaqMan Gene Express Assay (manufactured by Life Technologies)

TABLE 4

| Index | Gene name | TaqMan Assay ID |
|---|---|---|
| 1 | Era | Rn01640372_ml |
| 2 | Erb | Rn00562610_ml |
| 3 | PR-A | Rn01448227_ml |
| 4 | PR-B | Rn01448227_ml |
| 5 | Aromatase | Rn01422546_ml |
| 6 | VEGF | Rn01511601_ml |
| 7 | IL-6 | Rn01410330_ml |
| 8 | MCP-1 | Rn00580555_ml |
| 9 | PEDF | Rn00709999_ml |
| — | GAPDH | Rn01775763_ml |

[2] Methods for Conducting the Test
1. Total RNA Extraction
   RNA was extracted from the rat uterine horn strips and grafted uterine strip using the RNeasy Fibrous Tissue Mini Kit.
2. Quality Test of RNA with a Spectrophotometer and a Bioanalyzer
   Concentration of the extracted RNA was measured with a NanaoDrop. Also RIN measurements using a bioanalyzer (6000 nano kits) was carried out. A 6000 pico-kit was used for bioanalyzing of the two samples with low yield (Sample ID: 202, 507).
3. Reverse Transcription Reaction
(A) Standard Substance
   cDNA obtained by reverse transcription reaction from 1000 ng/uL of commercially available Rat Tissue Universal Reference Total RNA (Catalog Number PR-UR-100, ZYAGEN Inc.) using SuperScript VILO Master Mix (hereinafter "Standard") was used as a standard substance.
(B) Specimen
   Based on the concentration measured with a spectrophotometer, reverse transcription reaction of the specimen with Super Script VILO Master Mix was performed to give 50 ng/uL of cDNA (the following example). As for the samples with low yield, that is Sample ID: 202, 502, 507, the reverse transcription reaction was performed to give 25 ng/uL, 25 ng/uL, and 12.5 ng/uL of cDNA, respectively.
4. TaqMan Reaction
   TaqMan reaction by using Step One Plus Real-Time PCR System was performed with standard 250, 62.5, 15.625, 3.9, 0.98 ng/well or sample 5.0 ng/well. A cycle of reaction, two minutes at 50° C. and 10 minutes at 95° C., followed by 15 seconds at 95° C. and one minute at 60° C., was repeated 40 cycles, then the fluorescence value FAM was measured in real time after the reaction at 60° C. In addition to the target eight genes, GAPDH gene as an internal control gene was measured. All the standards and samples were measured in triplicate.
5. Gene Expression Quantification by Relative Standard Curve Method
   From each of the two calibration curves (target gene, GAPDH gene) obtained from the standard, gene expressions level of the target gene and GAPDH gene of the sample was calculated, respectively. Then, the target gene expression level was corrected by the GAPDH gene expression level, the internal control gene. And then, an average gene expression level of the samples in each group was calculated, followed by the average gene expression level of the two groups was used as a standard to compare with each of the other groups.

[3] Experiment Results
Target Gene Expression Analysis Results

TABLE 5

| Expression level ng | n | Era | Erb | PR | Aromatase | VEGF | IL-6 | MCP-1 | PEDF |
|---|---|---|---|---|---|---|---|---|---|
| Sham group | 3 | 55.5 ± 0.7 | 0.28 ± 0.03 | 248.5 ± 11.7 | — | 1.52 ± 0.12 | 0.71 ± 0.16 | 7.00 ± 1.16 | 2.77 ± 0.18 |
| E2 control | 6 | 44.2 ± 18.9 | 2.37 ± 1.07 | 101.0 ± 40.3 | — | 1.62 ± 0.43 | 14.24 ± 8.74 | 29.47 ± 20.81 | 4.51 ± 1.39 |
| SR 0.1 mg/kg | 6 | 39.3 ± 14.3 | 4.05 ± 1.88 | 94.6 ± 37.7 | — | 1.44 ± 0.43 | 9.77 ± 9.78 | 41.95 ± 21.68 | 6.44 ± 1.56 |
| SR 0.3 mg/kg | 6 | 47.6 ± 14.9 | 3.05 ± 1.02 | 176.2 ± 81.1 | — | 1.65 ± 0.40 | 6.01* ± 3.01 | 28.30 ± 10.93 | 6.62* ± 1.84 |
| SR 1 mg/kg | 6 | 33.2 ± 20.7 | 2.08 ± 1.51 | 127.8 ± 89.1 | — | 1.33 ± 0.57 | 6.74 ± 4.96 | 26.70 ± 18.30 | 5.93 ± 3.01 |

Figure 1:
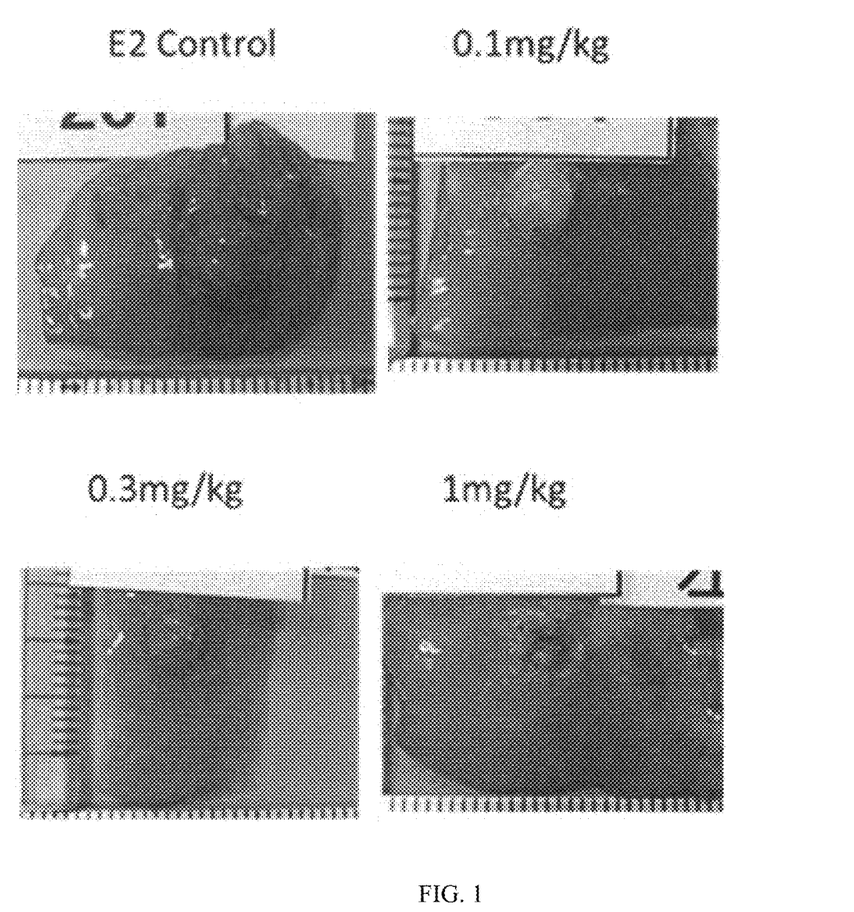
FIG. 1: A photograph showing grafted uterine strip of the rat endometriosis model in the examples.
Figure 2:
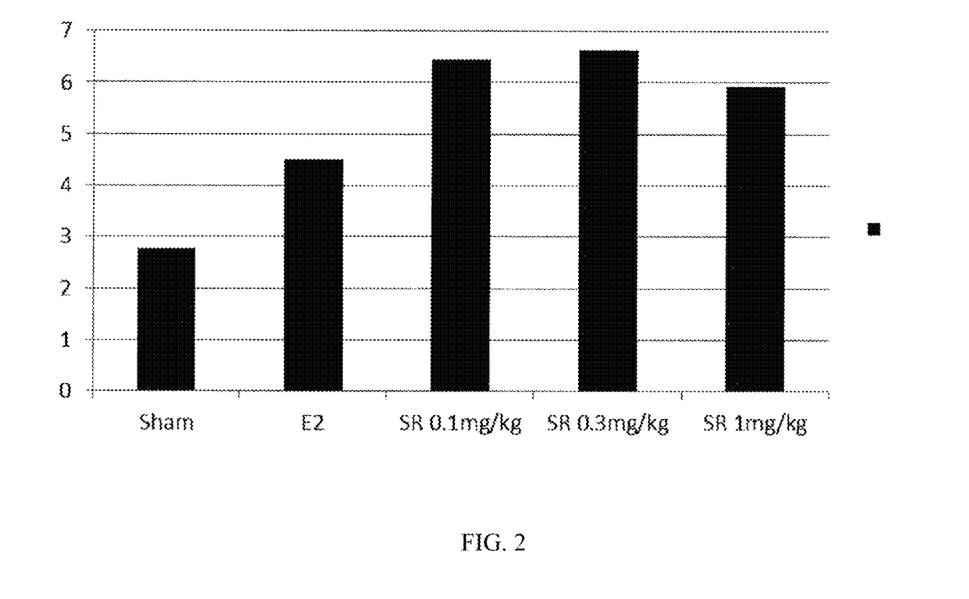
FIG. 2: A graph showing anti-angiogenic related PEDF gene expression promoting effect of the endometrial implants in the examples.
Figure 3:
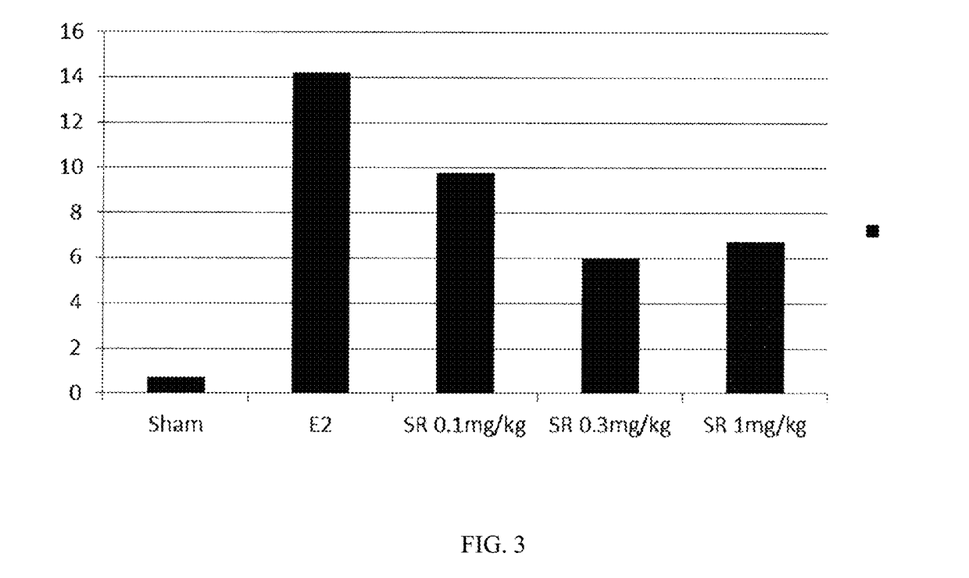
FIG. 3: A graph showing inflammation-associated IL-6 gene expression inhibitory effect of the endometrial implants in the examples.

In comparison with the E2 control group, the effect of SR16234 on the estrogen receptor gene expression of Era/Erb was not observed, and a slight increase trend was observed on the PR. No effect on the gene expression of VEGF relating to angiogenesis promotion was observed, but, as shown in FIG. 2, an increase trend was observed on the gene expression of PEDF, that is an angiogenesis inhibitor. Further, as shown in FIG. 3, the gene expression of IL-6, that is an inflammation related cytokine, was dose-dependently inhibited. These results on the gene expression illustrated that the drug had an inhibitory effect on inflammation associated with endometriosis, and angiogenesis.

INDUSTRIAL APPLICABILITY

The estrogen receptor α-inhibiting β partial agonist of the present invention can be administered orally with a low toxicity and safe anti-proliferative activity in ectopic endometrial tissues, thus it may be widely used as therapeutic agents for estrogen-dependent gynecological diseases such as endometriosis, uterine fibroids, and uterus adenomyosis.

The invention claimed is:

1. A method of treating a gynecological disease, comprising:
   administering an effective amount of a compound represented by following formula (a);

(a)

to a patient in need thereof,
wherein the gynecological disease is at least one disease selected from the group consisting of endometriosis, uterine fibroids, and uterus adenomyosis.

2. The method according to claim 1, wherein the compound is a pharmaceutically acceptable salt of the compound represented by the formula (a).

3. The method according to claim 2, wherein the pharmaceutically acceptable salts is at least one organic salt selected from the group consisting of citrate, fumarate, succinate, benzoate, and malonate.

4. The method according to claim 1, wherein the compound is an estrogen receptor β partial agonist having estrogen receptor α inhibitory effect.

* * * * *